United States Patent [19]

Rosa et al.

[11] Patent Number: 5,564,922
[45] Date of Patent: Oct. 15, 1996

[54] UNIVERSAL JOINT FOR DENTAL ABUTMENT IMPLANT

[76] Inventors: Michael F. Rosa, 3 The Hollows, Cuddington Lande, Cuddington, Northwich, Cheshire CW8 2SY; Malcolm P. J. Young, 6 Cranage Villas, Chester Road, Plumley, Cheshire WA16 OUB, both of Great Britain

[21] Appl. No.: 244,004

[22] PCT Filed: Nov. 12, 1992

[86] PCT No.: PCT/GB92/02096

§ 371 Date: Jun. 1, 1994

§ 102(e) Date: Jun. 1, 1994

[87] PCT Pub. No.: WO93/09728

PCT Pub. Date: May 27, 1993

[30] Foreign Application Priority Data

Nov. 16, 1991 [GB] United Kingdom .................. 9124417

[51] Int. Cl.⁶ ..................................................... A61C 8/00
[52] U.S. Cl. ........................................................ 433/173
[58] Field of Search ..................................... 433/173, 174, 433/175, 176, 201.1

[56] References Cited

U.S. PATENT DOCUMENTS

| | | | |
|---|---|---|---|
| 2,112,007 | 3/1938 | Adams | 433/174 |
| 3,732,621 | 5/1973 | Bostrom | 433/174 |
| 3,979,828 | 9/1976 | Taylor | 433/173 |
| 4,187,609 | 2/1980 | Edelman | 433/176 |
| 4,431,416 | 2/1984 | Niznick | 433/174 |
| 4,488,875 | 12/1984 | Niznick | 433/173 |
| 4,832,601 | 5/1989 | Linden | 433/173 |
| 4,842,518 | 6/1989 | Linkow et al. | 433/174 |
| 4,907,969 | 3/1990 | Ward | 433/173 |
| 4,932,868 | 6/1990 | Linkow et al. | 433/174 |
| 5,026,285 | 6/1991 | Durr et al. | 433/173 |
| 5,133,662 | 7/1992 | Metcalfe | 433/173 |
| 5,178,539 | 1/1993 | Peltier et al. | 433/173 |

FOREIGN PATENT DOCUMENTS

| | | | |
|---|---|---|---|
| 0288702 | 2/1988 | European Pat. Off. | 433/174 |
| 2655534 | 6/1991 | France | 433/176 |
| 2119258 | 11/1983 | United Kingdom | 433/173 |

Primary Examiner—John J. Wilson
Attorney, Agent, or Firm—Anthony J. Casella; Gerald E. Hespos

[57] ABSTRACT

A universal joint assembly for a dental abutment implant, comprising a support body which is adapted to be mounted within the alveolar bone of a patient, either directly or by way of an implant body, an abutment post fixed rigidly to a ball for the eventual support of a dental crown, and a generally annular securing means which embraces at least part of the ball and which can lock the ball in a selected attitude relative to the support body.

18 Claims, 10 Drawing Sheets

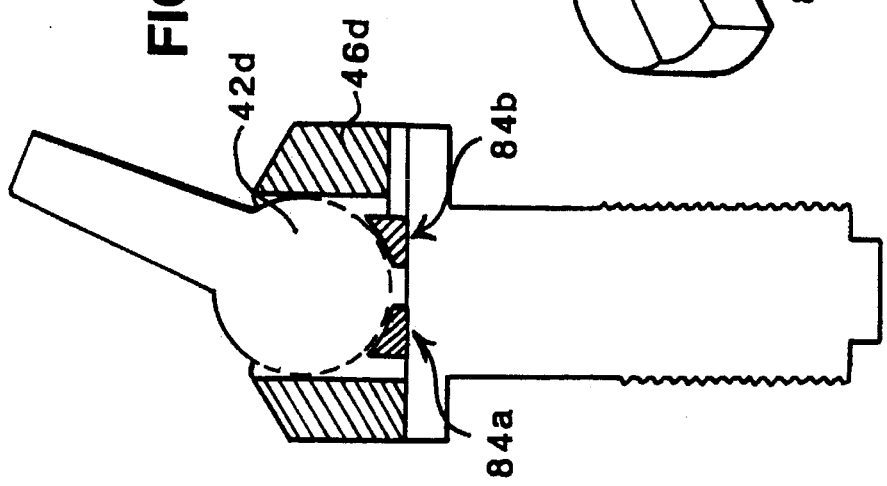
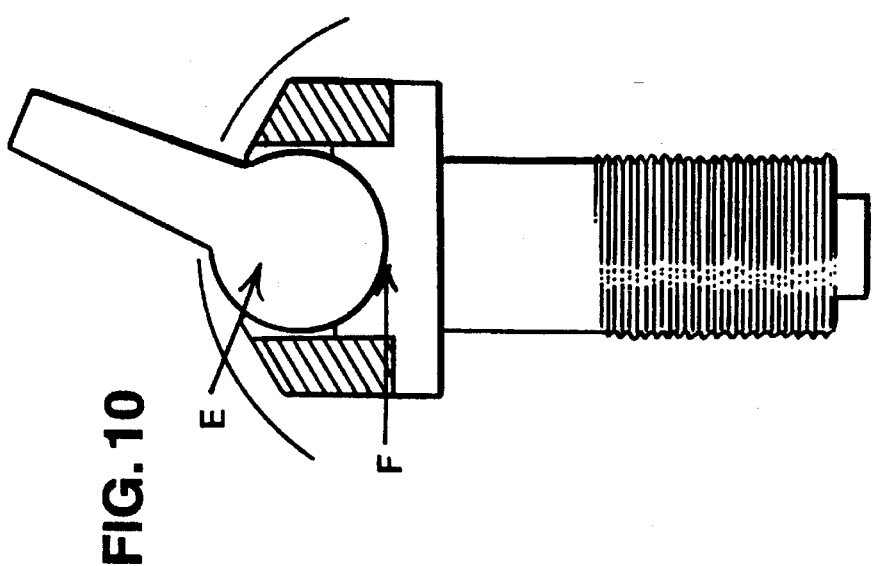

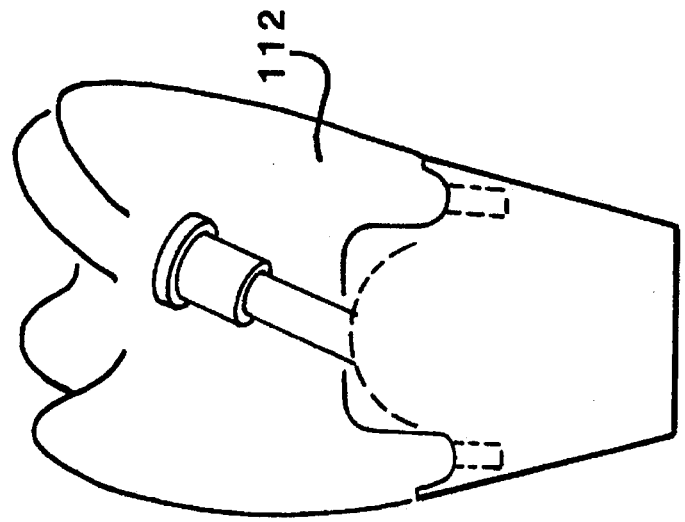
FIG. 21
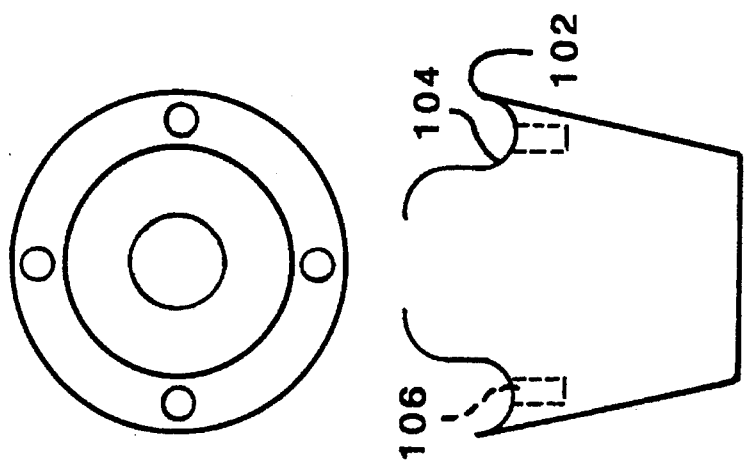
FIG. 19
FIG. 18
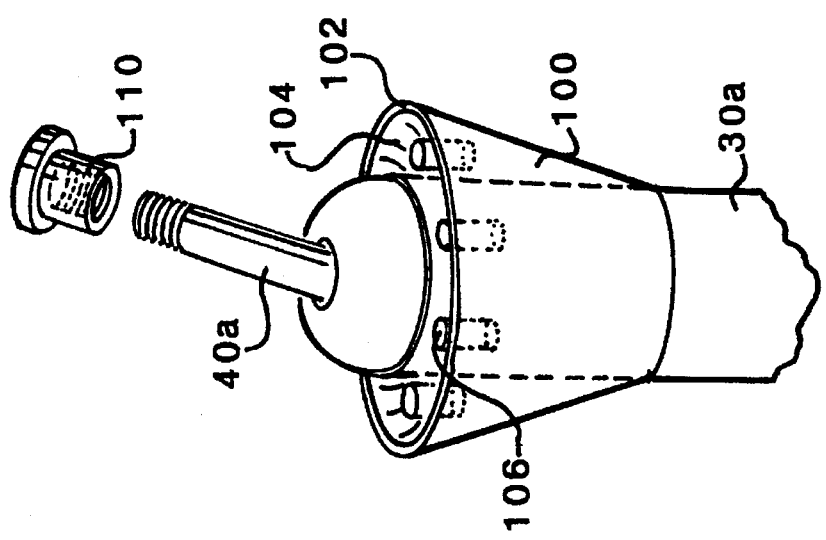
FIG. 20

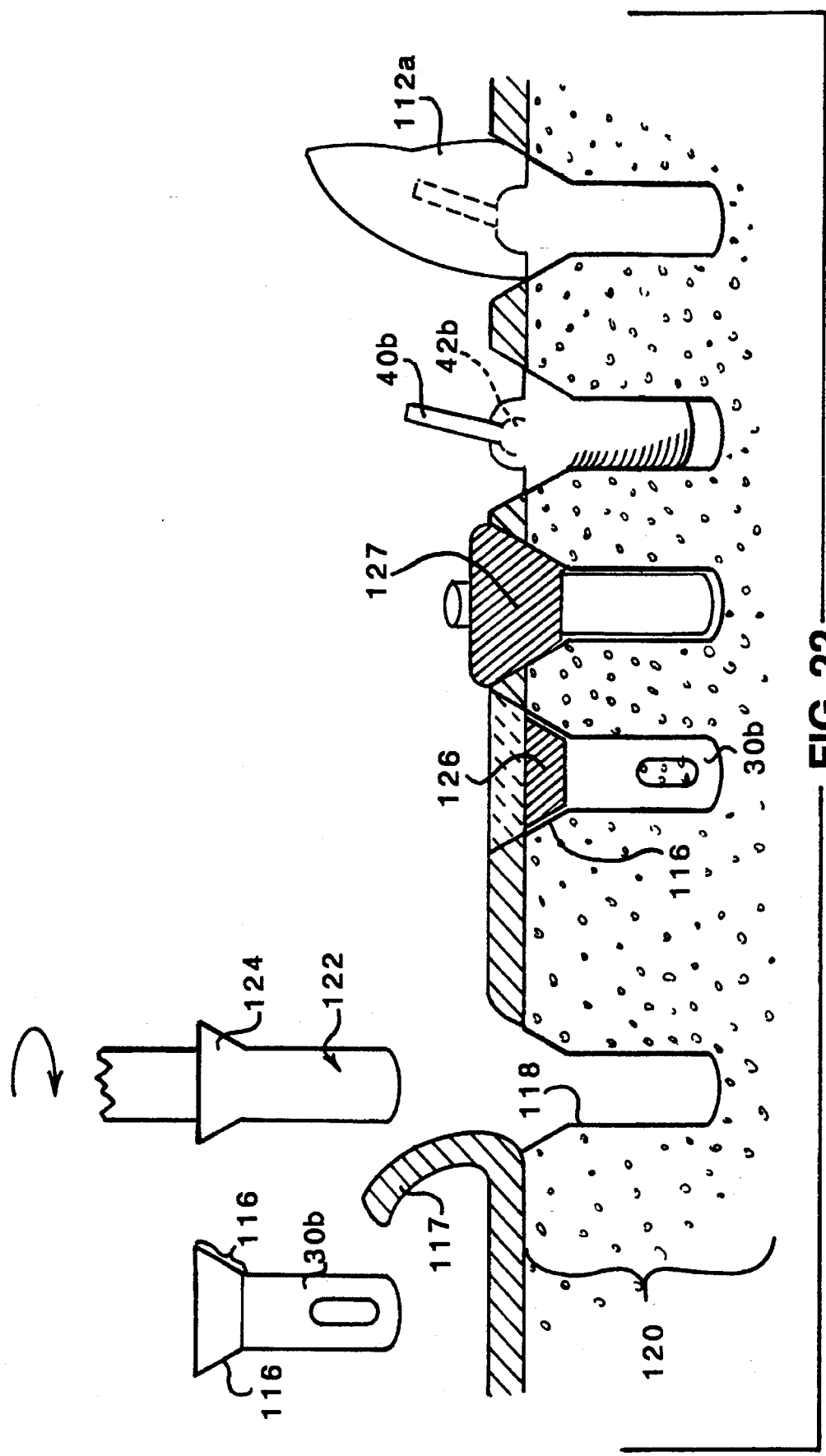

UNIVERSAL JOINT FOR DENTAL ABUTMENT IMPLANT

The present invention is concerned with a universal joint by which a dental abutment member, usually in the form of a post, can be coupled to a support member which, in use, is adapted to be implanted into the jaw of a patient.

It is well known in dental surgery to implant abutment posts into the jaw bone to provide anchor points for the location of individual artificial teeth, or sets of teeth, dental bridges and the like. In many situations, the dental surgeon wishes, for clinical reasons, to dispose the post in an attitude which is incompatible with the optimum implant direction within the jaw. For example, the optimum implant direction might be perpendicular to the jaw bone while the ideal attitude for the post, as far as a dental bridge to be supported thereby is concerned, is at some angle to the perpendicular.

It is already known in principle that this problem can be overcome by the use of a universal type joint arranged between the post and a separate, implanted body.

A known universal joint for this purpose is illustrated in FIG. 17 of the accompanying drawings and comprises a support member 10 which is adapted to be implanted into the jaw by a dental surgeon in a conventional manner. Screwed into the top of the support member 10 is a screw-threaded spigot 12 which has a ball portion 14 formed at that end which projects from the support member 10. The ball portion 14 of the spigot 12 is received within the hollow interior of an abutment post 16 and is forced against a reduced diameter, bevelled mouth 18 of the post 16 by means of a grub-screw 20 which engages a screw-thread 22 formed on the interior surface of the post 16. Initially, the grub-screw is removed from the post 16 and the ball portion 14 is therefore loose within the post. To assemble the joint in its operational position, the screw-threaded portion of the spigot 12 is first screwed into the support member 10, for example by means of a tool passed along the post 16. The grub-screw 20 is then inserted and partially tightened against the ball portion 14. With the components in this condition, the angle and attitude of the post 16 relative to the axis of the spigot 12 and support member 10 can be adjusted to comply with that required by the dental surgeon for correct fitting of the eventual denture to be mounted on that post. The grub-screw can then be further turned so as to force the ball portion 14 into abutment with the narrowed mouth portion 18 of the post 16 and thereby fix the components in that attitude. A mass 24 of suitable filler can later be added to fill up any space above the grub-screw 20, as shown in FIG. 17.

An important problem in practical use of the above described known joint is that a significant annular undercut area X is formed around the stem of the spigot 12, between the lower end of the post 16 (as viewed in FIG. 1) and the upper end of the support member 10. This annular area X provides a location where food debris, plaque and the like can collect and be very difficult to access and remove. These problems arise, inter alia, because (a) the ball 14 is rigidly fixed on the implanted support member 10, (b) the joint between the ball 14 and post 16 lies above the whole of the implant body, (c) the universality depends on the abutment post 16 rotating around the fixed ball, (d) the ball and abutment post are separate pieces, and (e) in all positions of the abutment post, undercuts are created which compromise oral hygiene. The result can thus be poor oral hygiene and, in some cases, severe gingival irritation which may lead to peri-implantitis and eventually even lead to the loss of the implant.

It is a principal object of the present invention to provide a universal joint structure which substantially eliminates this and other problems of the above described known device.

In accordance with the present invention in its broadest aspect, there is provided an assembly comprising a support body which is adapted to be received within an implant body, an abutment post fixed rigidly to a ball and a securing means which embraces the ball and which can lock the ball in a selected attitude relative to said support member.

In one preferred embodiment, the support member has a part-spherical recess at its emergent end and the securing means is adapted to co-operate with the support member to selectively clamp the ball to the latter recess.

In another embodiment the recess in the support body is conical.

The securing means can be in the form of an annular member, through which the abutment post/ball projects and which carries an internal thread which engages with an external thread on the support member. Advantageously, the annular securing means also has a part-spherical recess on its underside for engaging the ball. The co-operating surfaces of the ball and part-spherical recesses can be dimpled or otherwise roughened to increase the friction therebetween.

In another preferred embodiment, for uses in cases of severe angulation, the securing means can comprise a multipart arrangement including a first domed part having an eccentric aperture through which the abutment post/ball project and a second securing ring part which can selectively clamp the first, domed part to the support member.

In all cases, the external profile of the securing means is arranged to present a flush fit with the implant body when the assembly is inserted into its operational position. For the purpose, the external diameter of the securing means is preferably the same as that of the implant body.

In one embodiment, the support body is adapted to be mounted directly within the alveolar bone and itself defines an anvil against which the ball is urged by the securing means. Preferably, the support body comprises an elongate metallic member having an outwardly flared portion at its one end which receives the ball/abutment post, said outwardly flared portion having an internal screw-threaded recess into which the securing means can be screwed for securing the ball/abutment post to the support body.

In some embodiments the securing means can comprise an annular member through which the abutment post/ball projects and which carries an internal thread which engages with an external thread on the support member.

In other embodiments, the securing means can Comprise an annular member through which the abutment post/ball projects and which carries an external thread which engages with an internal thread on the support member.

By eliminating any significant recesses or undercuts between the abutment post and the support member, the problems of the known devices are similarly eliminated.

The invention is described further hereinafter, by way of example only, with reference to the accompanying drawings, in which:

FIGS. 7, 8, 9a, 9b, 10 to 11 illustrate alternative means of locking a selected orientation of the abutment component relative to the anvil component;

FIG. 18 is a diagrammatic sectional side view of another embodiment of securing cap component;

FIG. 19 is a plan view of the securing cap component of FIG. 18;

FIG. 20 is a perspective view showing the securing cap component of FIGS. 18 and 19, in use;

FIG. 21 is a diagrammatic side view showing a crown fitted to the assembly of FIG. 20;

Figure 23:
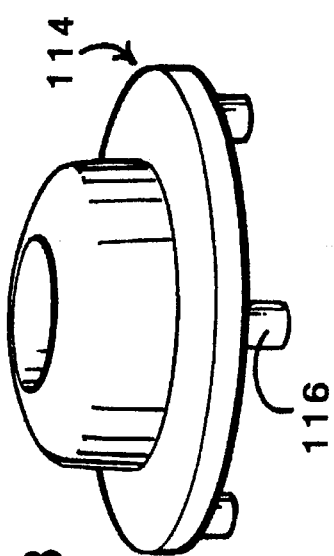
Figure 24:
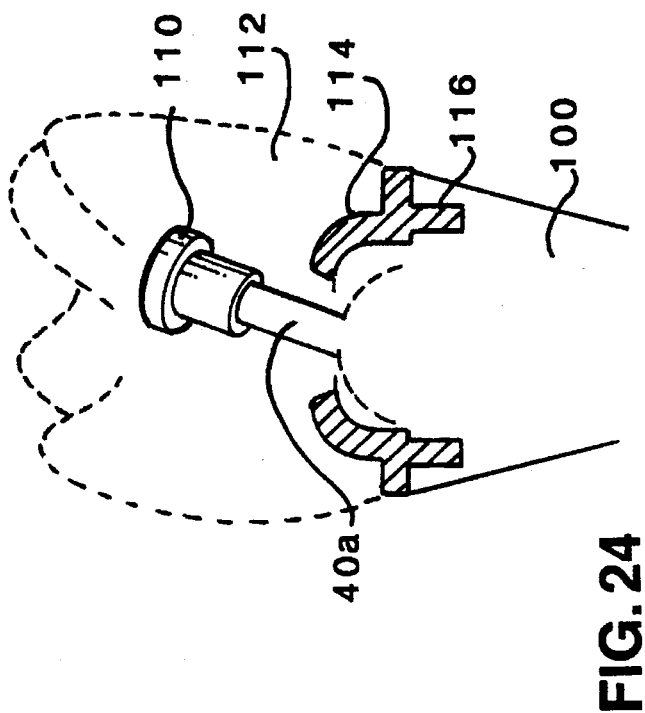
Figure 26:
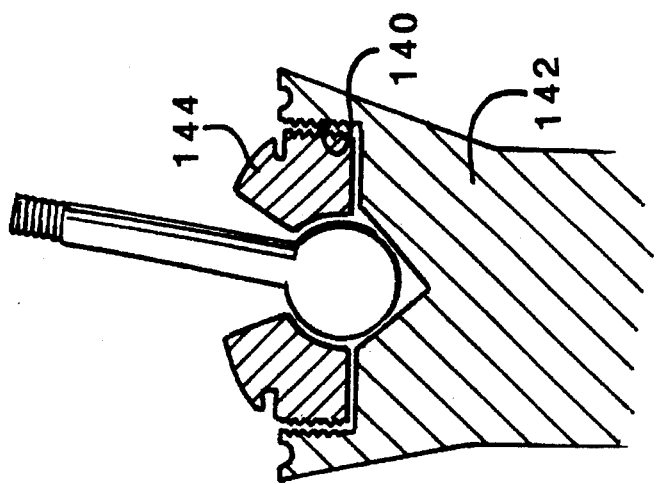
Figure 27:
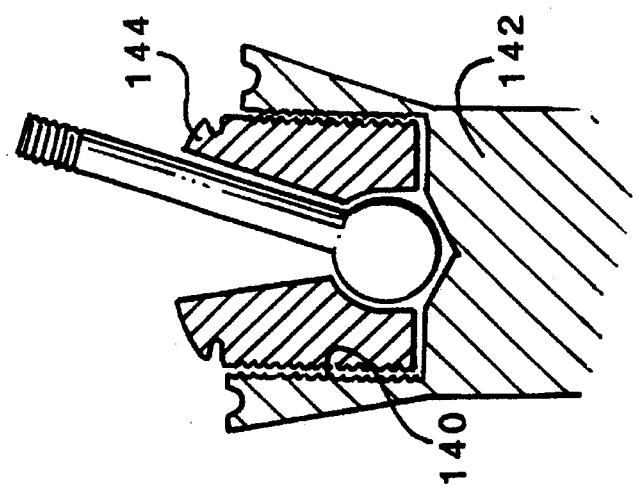
Figure 28:
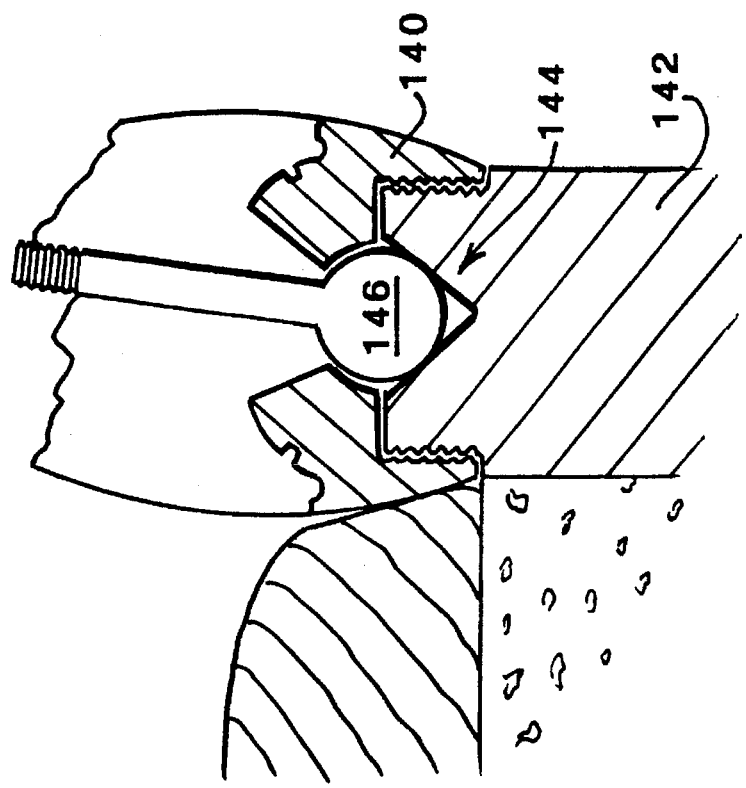
Figure 25:
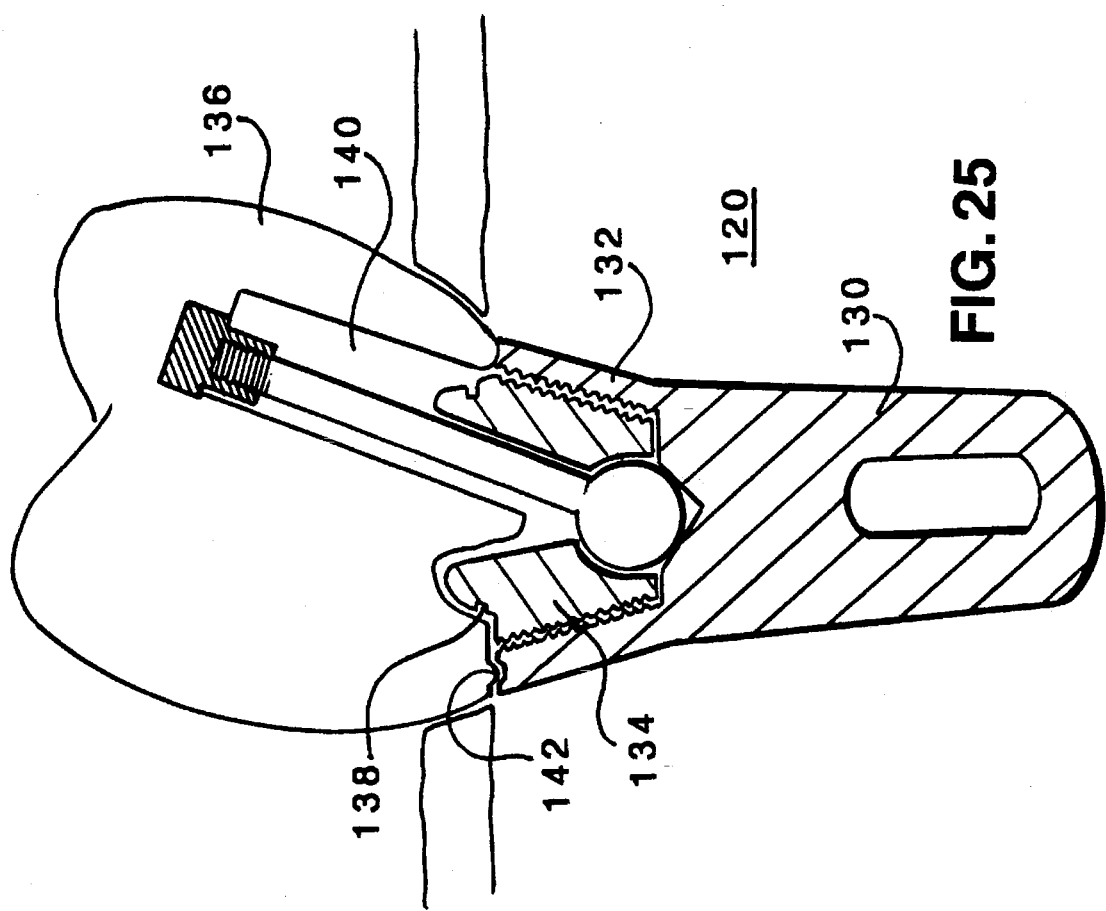

FIG. 22 comprises a series of diagrammatic side views illustrating the configuration and use of a modified implant body;

FIG. 23 is a perspective view of one embodiment of a damping member for use with an assembly in accordance with this invention;

FIG. 24 shows the damping member of FIG. 23 in its operational position;

FIGS. 25 is a partial section through another embodiment in accordance with the invention, fitted with a crown;

FIGS. 26 and 27 are partial sections through two further embodiments in accordance with the present invention; and FIG. 28 is a partial section through a still further embodiment in accordance with this invention.

Figure 2:
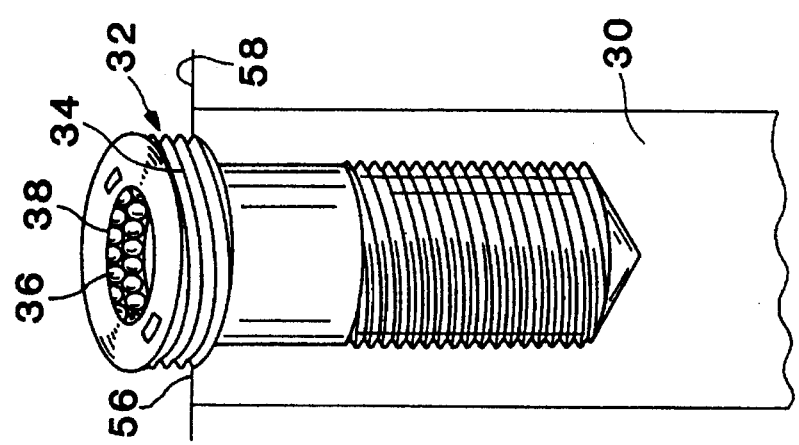
FIG. 2 shows the component of FIG. 1c when implanted in an operational position.
Figure 1C:
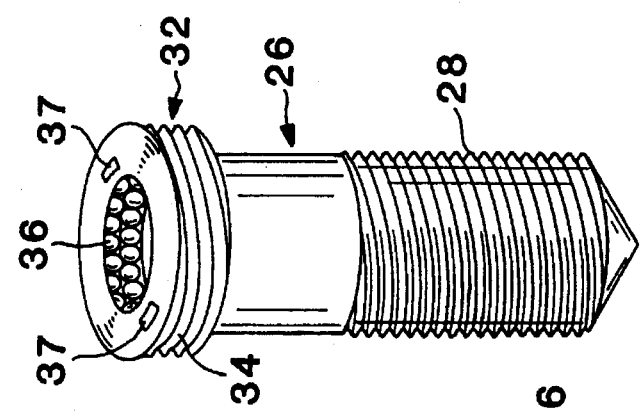
FIGS. 1a, 1b, 1c are perspective illustrations of the three principal components of a first embodiment of a universal abutment joint in accordance with the present invention.
Figure 1A:
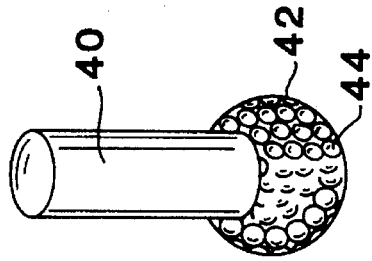
Figure 1B:
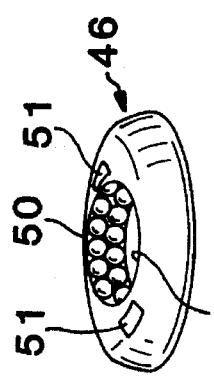

The components of FIGS. 1a, 1b and 1c assemble together to form a first embodiment in accordance with the present invention. The component of FIG. 1c comprises a support or "anvil" member 26 in the form of a cylindrical post having an external screw-threaded portion 28 extending from one end to enable the anvil member 26 to be fitted into a conventional hollow implant body 30, as shown in FIG. 2. The other end of the support member 26 has an integral head 32 of increased diameter provided with a peripheral screw-thread 34. The top surface of the support member head 32 (as viewed in FIG. 1c) is formed with a part-spherical recess 36 whose surface carries a plurality of positive dimples 38 or other means of providing an increased friction grip, such as a sandblast, grub-screw, microweld and the like (see later description of FIGS. 7 to 11). The top surface of the head 32 is also formed with a pair of integral securing recesses 37 which can receive a suitable tool for enabling the member 26 to be inserted rotatably into the implant body 30.

The component of FIG. 1a comprises a solid abutment post 40 rigidly connected, preferably integrally, at one end to a spherical ball 42. In this embodiment, the surface of the ball 42 is formed with a plurality of negative dimples 44 for co-operating with the positive dimples 38 of the support member 26.

The component of FIG. 1b is in the form of a securing cap 46 which is adapted to secure the post 40 to the support member 26. The securing cap 46 has a central aperture (see also FIG. 4) which defines a part-spherical surface 48 of the same diameter as that of the part-spherical recess of the support member 26. The surface 48 carries positive dimples 50 similar to the dimples 38. The securing cap 46 also has an internal thread 52 (FIG. 4) which is adapted to engage with the external screw thread 34 of the support member head 38, a pair of securing recesses 51 being disposed on the top of the cap 46 to enable it to be rotated into position.

Figure 3:
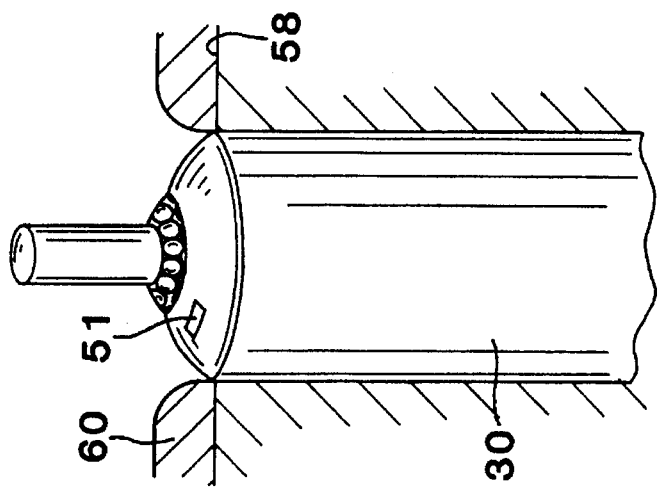
FIG. 3 shows all three components of FIGS. 1a, 1b and 1c when assembled together.
Figure 6:
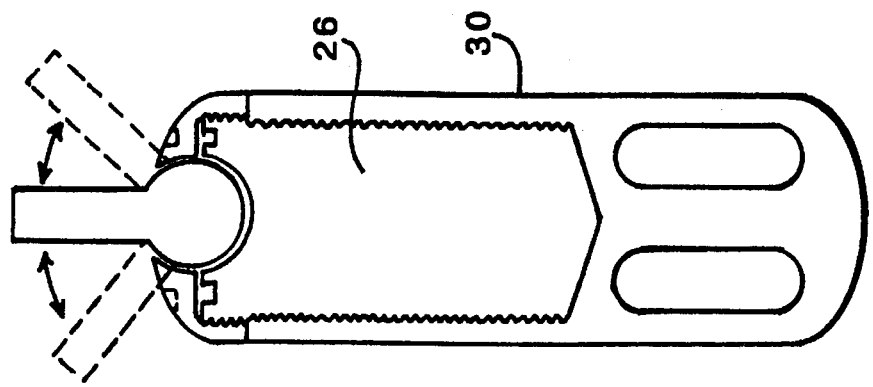
FIG. 6 is similar to FIG. 5 but illustrates the range of angular movement available for the abutment component.
Figure 5:
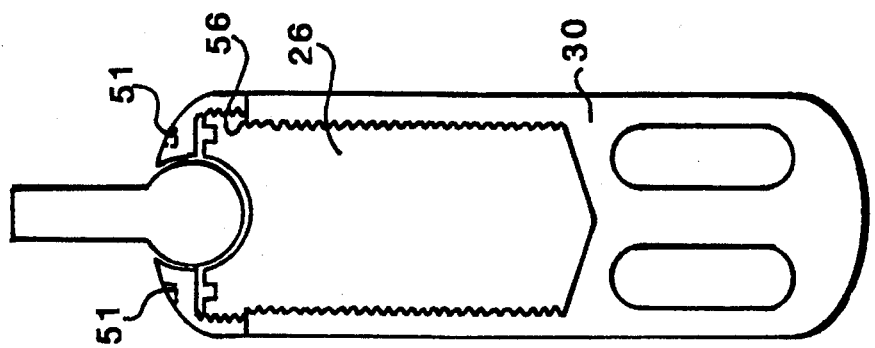
FIG. 5 is a longitudinal section through the assembled components.
Figure 4:
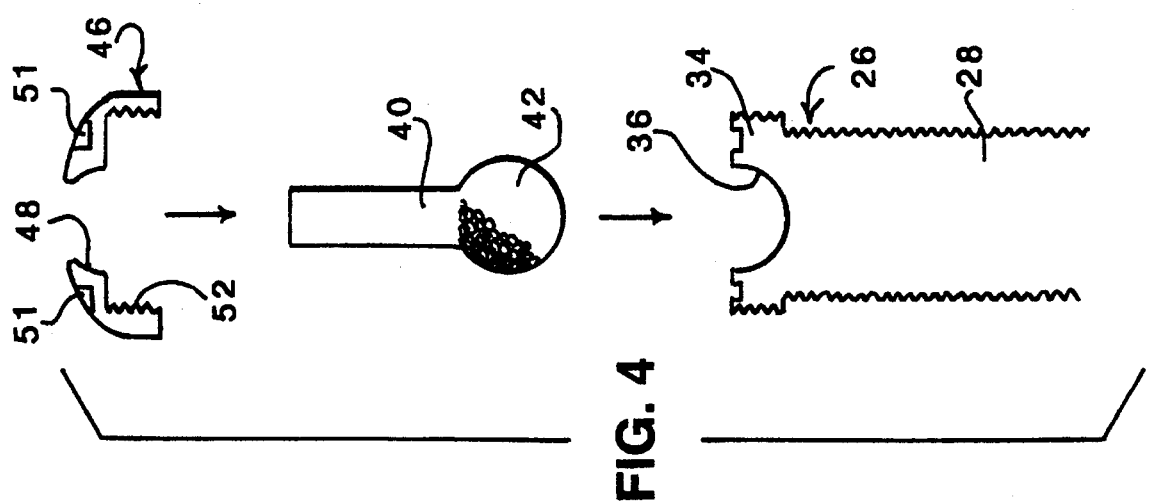
FIG. 4 illustrates diagrammatically the method of assembly of the components of FIGS. 1a, 1b and 1c.

Referring now more particularly to FIGS. 4 to 6, FIG. 4 shows how, in use, the ball 42 of the post 40 is presented to the part-spherical recess 36 of the support member 26 and the securing cap 46 is then applied over the post 40 and screwed to the support member 26 by the interengagement of the screw-threads 34, 52. Although not shown in FIG. 4, the support member 26 has already been screwed into a conventional cylindrical implant body 30, whose upper end surface 56 (as viewed in the drawings) is arranged to lie, substantially flush with the surface 58 of the jaw bone (alveolar), below the mucosa 60 (see FIG. 3). It will be appreciated from FIG. 3 that the securing cap 46 provides that part of the assembly which takes the implant from the bone level 58 to just above the mucosal level 60 and it therefore acts as a "transmucosal element" of the assembly. It will also be noted from FIGS. 3 and 5 that the outer diameter of the transmucosal securing cap 46 is the same as that of the implant body 30 and that there is a flush fit between these two components 30, 46 when the cap 46 has been screwed fully home onto the head 32 of the support member 26. Thus the transmucosal cap 46 presents a clinically sound shape to the gingeva whereby unwanted recesses which could collect food debris, plaque and the like are eliminated.

As illustrated in FIG. 6 prior to the transmucosal (securing cap 46 being fully tightened, the ball 42 can be rotated in any direction from the vertical position of FIG. 5 so as to achieve (within the limits set by engagement of the post 40 with the cap aperture 48) a desired angular orientation and thus a universal joint function. Once the desired angular orientation has been achieved, the securing cap is fully tightened against the support member 26 to fix the components securely in this orientation. The co-operation between the positive and negative dimples on these components serves to ensure that a permanent set is obtained.

It will be further noted that it is the rotation of the ball 42 and abutment post 40 together that allows the final angulation selection to be made, without comprising the clinical function of the transmucosal element in screening the universal joint, that is, the ball 42 remains in the same position inside the transmucosal element while the latter is rotating to secure the desired orientation. The ball joint is housed inside the transmucosal element 46 and rises vertically at the same angle as the implant body 30, to just above the mucosal level whereby to keep the transmucosal element/ball joint emergent profile clinically sound. The transmucosal element thus provides the triple function of permitting adjustment of the angulation of the abutment post 40 and housing the universal ball joint, whilst clinically separating the universal joint components from the surrounding mucosa. The fixing recesses 51 on the cap 46 can be filled with suitable filler.

FIGS. 7 to 11 show diagrammatically a number of other means which can be used to lock the set position of the ball joint as an alternative to the use of the abutting dimples 38, 44, 50. These are described very briefly hereinafter.

Figure 7:
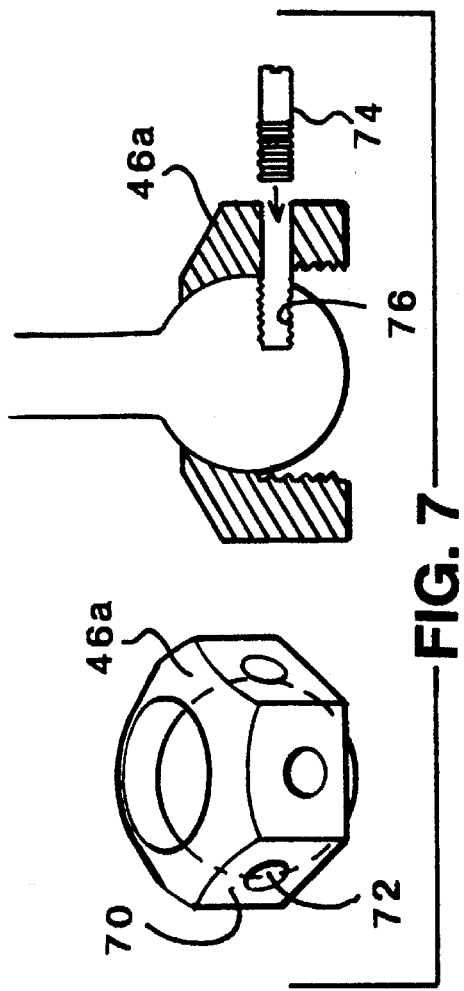

In the embodiment of FIG. 7, the transmucosal cap 46a is formed with a plurality of flats 70, each of which contains a through hole 72. When the desired angulated position of the ball 42a and post 40a has been set, a hole 76 is drilled into the ball via one of the holes 72 and formed with an internal thread. A grub-screw 74 is then inserted through that hole 72 into the tapped hole 76 to secure the selected orientation. The unused holes 72 need to be filled with a suitable filler.

Figure 8:
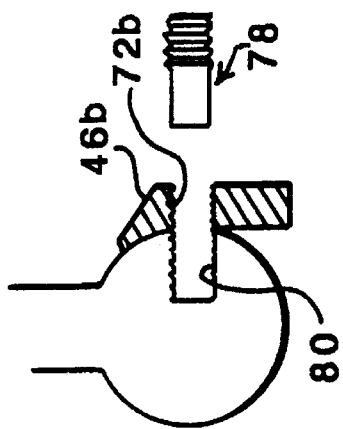

A modification of the latter embodiment is illustrated in FIG. 8 where the holes 72b in the cap 46b are themselves threaded and the grub-screw has a non-threaded leading end 78 which is adapted to be inserted into a plain bore 80 in the ball.

In another embodiment, the ball can be covered in a suitable solder and joined to the surrounding components in the selected orientation simply by heating. One method of achieving this is shown diagrammatically in FIG. 10. In this case the ball and/or part-spherical support member seat can be applied with a suitable solder (for example a silver solder applied by spraying) where indicated at E and F, respectively. Once the optimum angular position of the post has been set, the assembly comprising the support member, securing cap, and ball and post can be removed as one piece and held in a Bunsen flame to allow the solder to flow. The assembly is then screwed back into place.

Figure 9A:
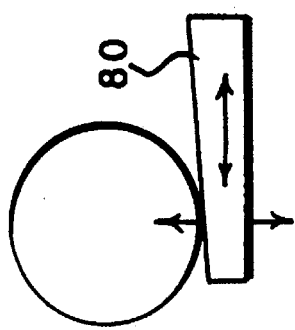
Figure 9B:
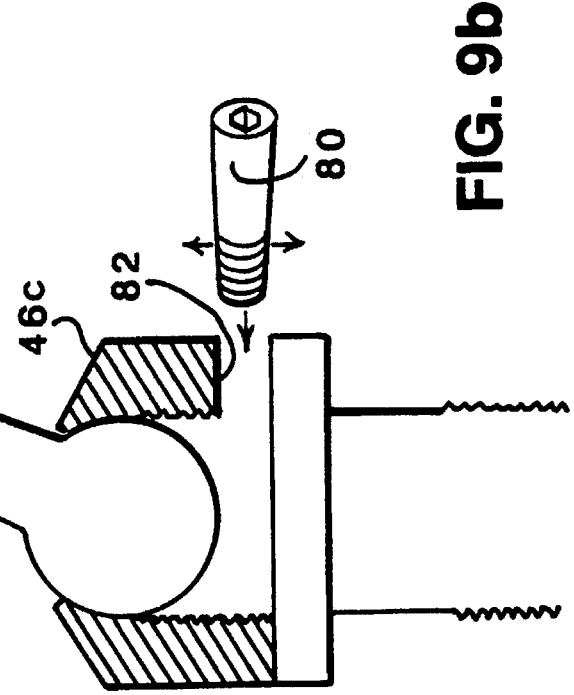

FIGS. 9a and 9b illustrate an embodiment using a tapered screw 80 which is inserted into a tapped hole 82 in the cap 46c such that upward pressure is exerted on the ball as the tapered screw is driven under the ball. The ball is thereby urged upwardly against a tapered opening in the cap 46c to eventually lock the ball in position.

The embodiment of FIG. 11 uses a pair of identical shims 84a, 84b having respective screw-threaded bores 86a, 86b through which a common Allen bolt 88 can be driven. The threads on the shims/bolts are such that rotation of the bolt 88 causes the shims 84a, 84b to move together, thereby pushing the ball 42d upwards against the underside of the mouth of the securing cap 46d.

The remaining FIGS. 12 to 16 relate to an embodiment which can be used in the case of severe angulation where the desired angle of the post 40 relative to the longitudinal axis of the support member/implant body exceeds that which is available for the embodiments described thus far.

Figure 12:
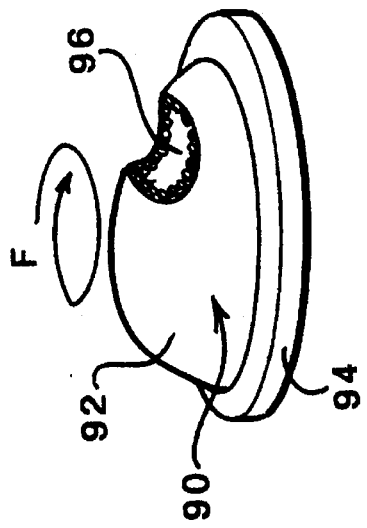
FIG. 12 is a perspective view of an alternative securing cap component which can be used in cases of severe angulation of the abutment post.
Figure 13:
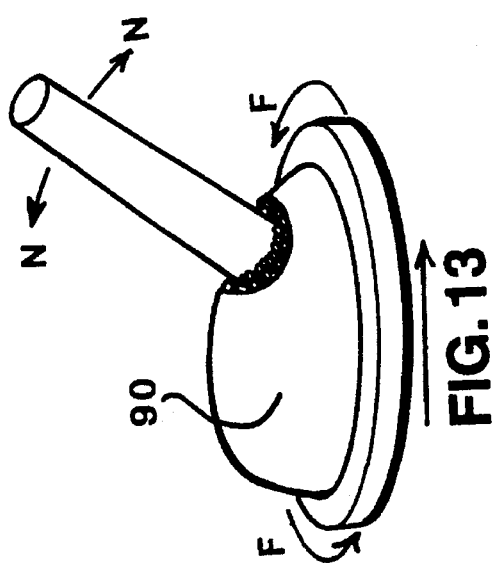
FIG. 13 shows the cap of FIG. 12 with the abutment post extending therefrom.
Figure 17:
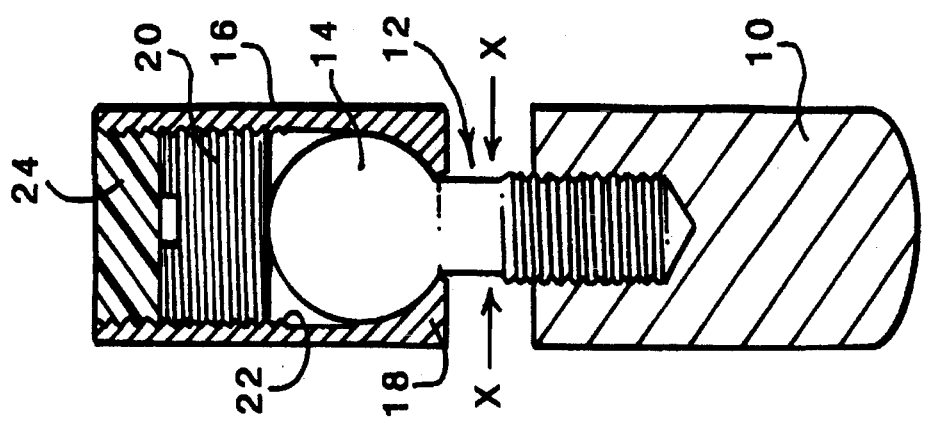
FIG. 17 is a diagrammatic sectional view through a known universal joint assembly.
Figure 14:
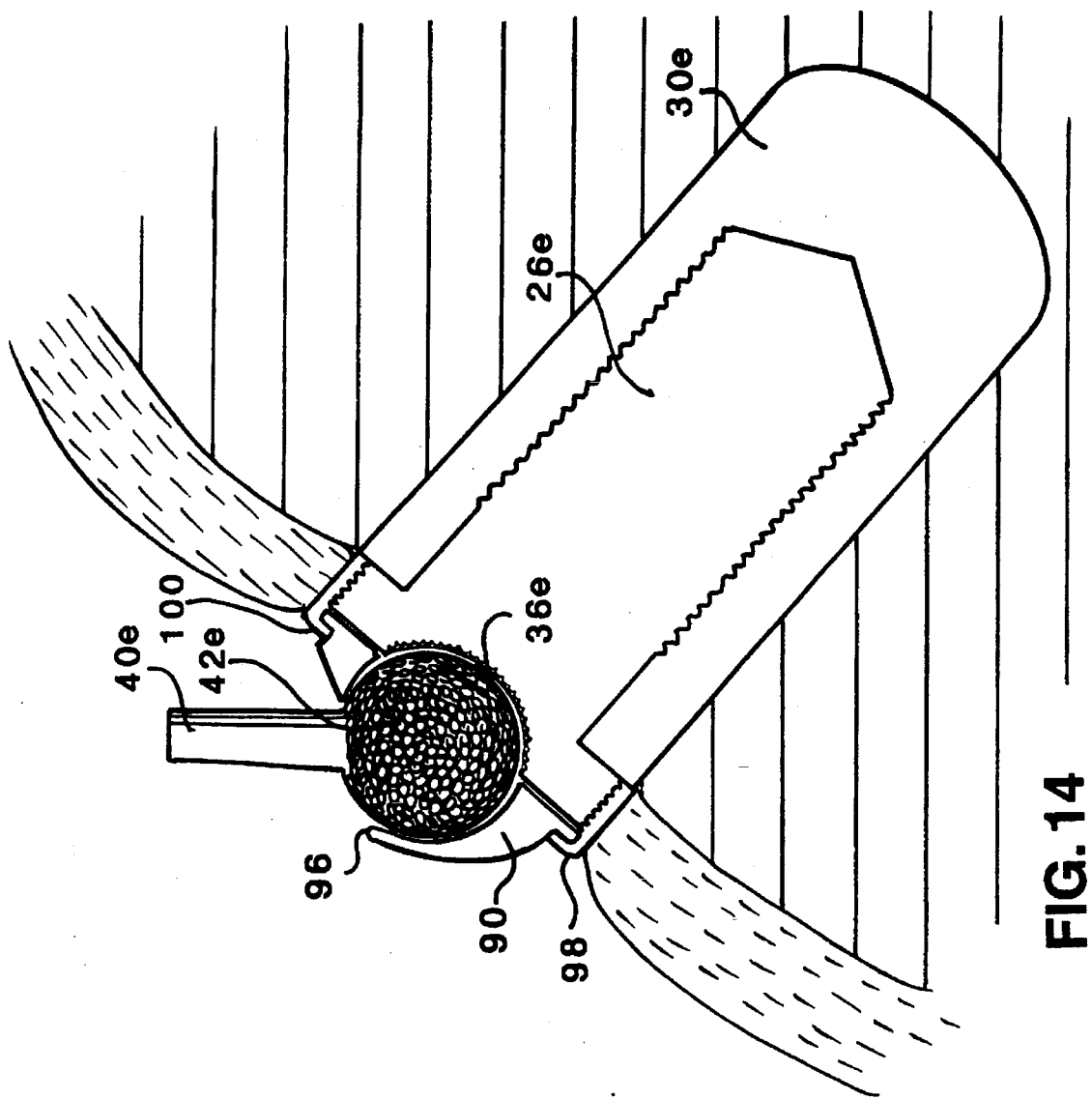
FIG. 14 is a sectional view of an assembly using the securing cap of FIGS. 12 and 13.

As shown in FIGS. 12, 13 and 14, this embodiment makes use of a modified securing arrangement where the securing cap 46 of the earlier embodiments is replaced by a two-part assembly consisting of a first component 90 having a hollow domed part 92 and a peripheral flange 94. The domed part contains an eccentric hole 96 which connects interiorly with a part-spherical recess for engaging a major portion of a ball 42e attached to an abutment post 40e. The second component of the two-part assembly is an internally threaded securing ring 98 which is adapted to engage has an inwardly directed peripheral lip 100 which engages over the flange 94 of the domed part 92 for holding it in place.

As shown in FIG. 14, the domed part and the securing ring are shaped so as at all positions to present as smooth and flush a joint between them as possible, so as to minimise the formation of cavities or recesses where debris could lodge. Thus, the contour presented to the surrounding gingiva is substantially uninterrupted and hence gingival irritation is minimised.

The assembly of the embodiment of FIG. 14 is as follows. The support member 26e is first screwed into position in the already inserted implant body 30e. The ball 42e is presented to the recess 36e in the support member and the domed component is placed over the ball so that the post 40e projects through the eccentric hole therein. The securing ring is placed over the flange 94 and partially screwed up. The domed component (and with it the ball and abutment post) are then rotated as illustrated in FIGS. 12 and 13 by arrows F, and the angular orientation of the post adjusted as illustrated by arrows H, until the desired position of the post has been achieved. Finally, the securing ring is tightened by a suitable tool until locking occurs. A secure fit can again be obtained by dimpling the abutting surfaces.

Figure 16:
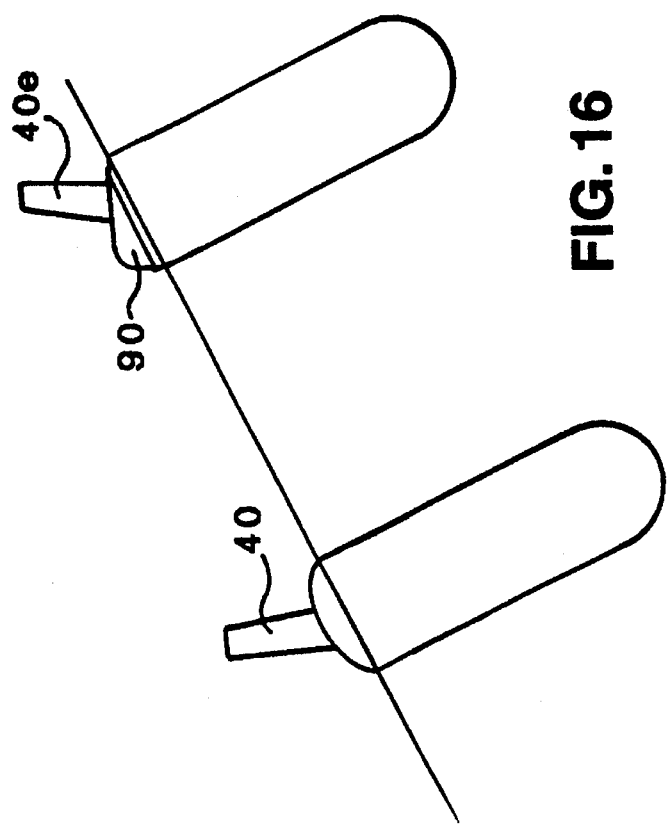
FIG. 16 illustrates two implants in identical orientations, one having the standard securing cap of FIG. 1b and the other the severe angulation cap of FIG. 12.

FIG. 16 illustrates how for identical angulations of the implant bodies, the component of FIG. 14 (right-hand in FIG. 16) provides a better clinical platform for the ensuing superstructure (not shown) than the component of FIGS. 1 to 6 (left-hand in FIG. 16).

Figure 15:
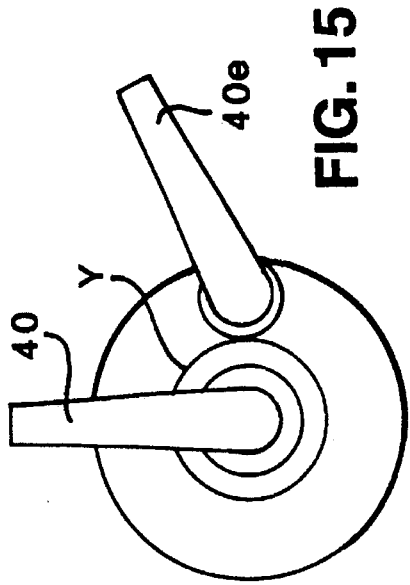
FIG. 15 is a diagrammatic illustration of the differences between an assembly using a "standard" closure cap of FIG. 1b compared to the severe angulation cap of FIG. 12.

FIG. 15 is a diagrammatic plan view showing the embodiment of FIGS. 1 to 6 superimposed on the embodiment of FIG. 14 to demonstrate how the basic version of FIGS. 1 to 6 will cater for most angulations met in practice but how, where the angle exceeds that in which the post 40 will engage the circle marked Y, the severe angulation version of FIG. 14 must be used.

Referring now to FIGS. 18 to 21, there is shown a modified version of the securing cap having an outer body 100 that is flared outwards towards its upper end to define a generally horizontal shelf 102. The shelf is profiled so as to define an annular trough 104 of part circular section extending around the periphery of the body 100. The base of the trough contains a plurality of bores 106 which, in this embodiment are cylindrical. In other embodiments, some of the bores can be of different shapes, e.g. laterally elongated. The bores 106 are adapted to receive projections on a suitable tool for use in rotating the securing cap relative to the implant member (not shown in these Figures) into its operational position. In the same manner as in the first-described embodiments, the securing cap 100 is arranged to hold the ball of an abutment post 40a against an anvil member (not visible in FIGS. 18 to 21) embedded in the implant body (30a).

In this particular embodiment (FIGS. 20 and 21), the abutment post 40a is threaded at its free end and carries an internally screw-threaded nut 110 which has a wider diameter head for enabling it to be more easily gripped for tightening purposes. Fewer or more bore holes 106 than the four shown in FIG. 19 can be used, depending on the abutment angle.

In use of the latter embodiment the anvil member (not shown) is first screwed into the implant body and tightened using a suitable tool. The abutment post 40a is passed through the cap 100 and the latter cap is then tightened, when the final position angle of the abutment post has been selected, using a tool which engages the bores 106 in the trough. A dental impression is taken (which might use cylindrical rods (not shown) placed in the bores 106 to be picked up by the impression).

With the aid of suitable laboratory analogs, a crown 112 can then be constructed. As illustrated in FIG. 21, the crown 112 will engage over the abutment post 40a and fit precisely into place into the trough 104 and bore holes 106. When the crown is in place, the abutment screw nut 110 can be screwed into a flush position on the crown and tightened to hold the crown in its operational position. The crown can be released, when desired, by removal of the nut 110. The trough 104 and bores 106 assist in providing adequate retention to oppose oral displacement forces.

FIGS. 23 and 24 show an embodiment of renewable shock-absorber pad 114 made of a resilient material and which can be located between the crown 112 and the securing cap 100. Projections 116 on the shock absorber pad 114 can engage in the bores 106 for location purposes.

In a further modification of the embodiment of FIGS. 18–21, the cylindrical part of the abutment post can be provided with a longitudinal groove to provide extra resistance to oral forces which seek to rotationally dislodge the crown. The crown would have a corresponding male counterpart to engage this groove in this embodiment.

Although shown in FIGS. 18 to 21 as being at the bottom of the annular trough 104, in still further embodiments the horizontal shelf 102 containing the bores 106 can be flat (no trough).

In the embodiment of FIGS. 18 to 21, the outer side wall of the body of the securing cap is frustoconical, i.e. the taper of the side wall is constant along its length. In other embodiments, this side wall can be curved so as to be flared outwardly towards its upper end (considered in the direction as viewed in FIG. 18).

With reference now to FIG. 22, there is shown a series of assembly stages when using a modified form of implant body which allows the universal joint of the present invention to be placed in a lowered osteo/mucosal position whereby the universal joint can be used in situations where the mucosal thickness is 2 mm or less, thereby achieving better aesthetics at the cervical margin for the crown. This lowered position is achieved using an implant body 30b having a flared dished head 116, preferably made of highly polished titanium to aid osteo integration and acting as a dieback collar.

The correct shaped hole 118 in the alveolar bone 120 for this new implant 30b is made using a cannon type burr 122. The corresponding flare 124 on the burr 122 enables the flared dished head 116 of the implant to be countersunk into the bone 120. Different size (diameter and length) can be selected according to situational conditions dictating the required size of implants.

In practise of such a technique, the correct flared cannon burr 122 is selected and, after peeling back a mucosal flap 117, a hole 118 drilled in the alveolar bone 120 site to produce a neatly countersunk hole. The surgeon then places the implant 30b into position in the hole 118 and seals the top with a submucosal "healing screw" 126 which allows the implant to osteo integrate. Three to six months later, the healing screw 126 is removed. A healing cap 127 is now inserted into the implant to establish the mucosal implant interface. The healing cap 127 is eventually removed and the anvil is screwed into the implant body as in abovedescribed embodiments. The ball 42b and abutment post 40b is then placed in position and the securing cap tightened over to its full locking position once the optimum abutment angle has been selected. The outer wall of the securing cap marries perfectly with the inner wall of the flared dish portion of the implant. The crown 112a is then made and secured in position as described hereinbefore.

FIGS. 25 to 28 illustrate further embodiments which are modified in that the anvil part is manufactured integrally with the implant body. Referring first to FIG. 25, there is shown a combined anvil/implant 130 having a flared upper end 132. This is fitted within a bore in the alveolar bone 120 in the same manner as in FIG. 22, using the special cannon burr 122. In this case, a securing cap 134 is located internally of the flared part of the implant body 130 whereby to be positioned (subosseously) below the bone surface. A crown 136 is then built on the post in the manner described for other embodiments, but preferably with a mesostructure 140 of cast metal therebeneath. Locking recesses 138 can be provided on the securing cap 134 where shown for engagement by a suitable locking spanner 140. Further recesses 142 can be provided in the top surface of the implant 130 for receiving corresponding male projections on,the crown 136. By virtue of this arrangement, potential superstructure undercuts, which might otherwise exist, are eliminated since the abutment post always makes just one angle relative to the mucosal horizon. Furthermore, the presence of submucosal porcelain (of the crown) is guaranteed, so that gum recession will lead to exposure of further porcelain and not implant body.

Since it employs tapered intermeshing threads on the implant and securing cap, the embodiment of FIG. 25 is complicated to manufacture. In the embodiment of FIGS. 26 and 27, therefore, the threaded bore 140 in the implant body 142 which receives the securing cap 144, and the securing cap itself, are cylindrical. The same goes for the embodiment of FIG. 26. The latter embodiment (FIG. 26) shows how the ball can be raised or lowered by lifting the height of the integral anvil, at the implant manufacture stage. In both examples of FIGS. 26 and 27, the implant is osteo integrated, as in the examples of FIGS. 22 to 25.

Referring finally to FIG. 28, there is shown a variation which uses an integral anvil design but a non-osteo integrated securing cap. In this case, the cap 140 is a flush fit with the implant body 142, the implant having an integral anvil 144. The cap 140 screws over the outer wall of a screw-threaded upper portion of the implant body 142 to secure the ball 146 in position when fully screwed home flush with the implant body.

Although as described above the post 40 and ball 42 can be integral, in all embodiments the post can equally well be a screw fit in a threaded recess/bore in the ball. This can be useful in that it permits, for example, the following procedure. The universal joint (or joints) can be tightened to achieve the selected abutment angle(s). The abutment posts 40 can then be screwed out of the ball(s) 42 and replaced temporarily with plastics or alloy rods. A dental impression is then taken, picking up the dummy rod(s) or laboratory analogs. This is sent to the laboratory and a stone model is cast. The laboratory would thus use this to construct the crown or bridge following conventional techniques. When returned to the surgery, the original abutment post(s) would be screwed back into the located ball. The crown or bridge would be placed on top and secured in position, for example using the screw nut 110. Alternatively, the post 40 could carry a slotted head or simply have a slotted end to enable it to be rotated by a screwdriver-like tool.

We claim:

1. A universal joint assembly for a dental abutment implant, comprising:

an elongate, generally cylindrical support body which is adapted to be mounted within the alveolar bone of a patient so as to leave one axial end face thereof exposed from said bone, means defining an internally, threaded cavity within said one end face of said support body such that there remains an annular surface portion of said one end face around said cavity, said annular portion of said one end face of the support body defining a tooth receiving surface on which, in use, a tooth is received;

an abutment post fixed rigidly to a ball, said ball abutting a portion of said support body within said cavity and said abutment post projecting through said cavity and beyond said tooth receiving surface for mounting in the tooth; and an annular securing means having a distal end and an opposed proximal end which embraces at least part of the ball, and external screw-thread means on said annular securing means between said proximal and distal ends which are in threaded engagement with said internally threaded cavity of said support body for locking said ball in a selected attitude relative to said support body, a central aperture extending through the annular securing means such that the abutment post extends through the aperture for mounting in the tooth.

2. An assembly as claimed in claim 1, wherein said recess is conical.

3. An assembly as claimed in claim 1, in which the support body defines an anvil against which the ball is urged by the securing means.

4. An assembly as in claim 3, wherein the support body comprises an elongate metallic member having an outwardly flared portion at its one end which receives the ball of the abutment post, said outwardly flared portion having the internally threaded cavity into which the securing means can be screwed for securing the ball of the abutment post to the support body.

5. An assembly as claimed in claim 1 in which the annular securing means has a part-spherical recess on its underside for engaging the ball.

6. An assembly as claimed in claim 5, in which the co-operating surfaces of the ball and part-spherical recess on the securing means are non-smooth so as to increase the friction therebetween.

7. An assembly as claimed in claim 1, in which the abutment post is screw-threaded at
one end and is received with a correspondingly screw-threaded bore in the ball to enable the ball and abutment post to be rigidly fixed together in a releasable manner.

8. An assembly according to claim 1 in which said generally cylindrical support body is of frusto-conical external configuration at its end adjacent said one axial end face.

9. An assembly according to claim 1 in which said annular portion of said one end face of the support body which defines said tooth receiving surface is flat.

10. An assembly according to claim 1 in which said annular portion of said one end face of the support body, which defines said tooth receiving surface, contains an annular circumferential recess.

11. An assembly according to claim 1, wherein said internally threaded cavity with said one end face of the support body contains a conical recess defining a ball receiving surface against which said ball is urged by means of said annular securing means.

12. An assembly according to claim 1 in which said central aperture of said annular securing means is flared at the distal end to enable alignment of the abutment post at the selected attitude relative to the support body.

13. An assembly as claimed in claim 12, wherein said recess is part-spherical.

14. An assembly as claimed in claim 12, in which the support body is adapted to be mounted in the alveolar bone by way of a separate implant body member which is itself adapted to be located within a hole in the alveolar bone, the support body being screwed into said implant body.

15. An assembly as claimed in claim 14, wherein the securing means comprises an annular cap having a body portion which is flared outwardly towards one end, the flared portion defining a radial shoulder portion containing a plurality of bores for use in rotating the securing member into its operational position on said implant body member.

16. An assembly according to claim 15, for use in cases of sever angulation, wherein the securing means comprises a multi-part arrangement, including a first domed part having an eccentric aperture from which said post projects and a second securing ring part which selectively clamps the first, domed part to the support body.

17. An assembly according to claim 15 wherein the ball engaging surface of the securing means and the ball receiving surface of the securing means and the ball receiving surface of the support body are non-smooth so as to increase the friction between these surfaces and said ball.

18. A universal joint assembly for a dental abutment implant, comprising a support body which is adapted to be mounted within the alveolar bone of a patient, an abutment post fixed rigidly to a ball and a securing means which embraces at least part of the ball for locking the ball in a selected attitude relative to said support body, said securing means comprising a plurality of parts, including a first domed part having an eccentric aperture through which the abutment post projects and a second securing ring part selectively clamping the first domed part to the support member.

* * * * *